US012225888B2

(12) United States Patent
Blake et al.

(10) Patent No.: US 12,225,888 B2
(45) Date of Patent: Feb. 18, 2025

(54) TRANSGENIC RAINBOW SHARK

(71) Applicant: GloFish, LLC, Earth City, MO (US)

(72) Inventors: Alan Blake, Austin, TX (US); Richard Crockett, Wilton, CT (US); Aidas Nasevicius, Tampa, FL (US)

(73) Assignee: GLOFISH, LLC, Earth City, MO (US)

( * ) Notice: Subject to any disclaimer, the term of this patent is extended or adjusted under 35 U.S.C. 154(b) by 554 days.

(21) Appl. No.: 16/961,195

(22) PCT Filed: Jan. 10, 2019

(86) PCT No.: PCT/US2019/013072
§ 371 (c)(1),
(2) Date: Jul. 9, 2020

(87) PCT Pub. No.: WO2019/140103
PCT Pub. Date: Jul. 18, 2019

(65) Prior Publication Data
US 2021/0051927 A1 Feb. 25, 2021

Related U.S. Application Data

(60) Provisional application No. 62/615,638, filed on Jan. 10, 2018, provisional application No. 62/615,634, filed on Jan. 10, 2018, provisional application No. 62/615,628, filed on Jan. 10, 2018, provisional application No. 62/615,625, filed on Jan. 10, 2018.

(51) Int. Cl.
*A01K 67/027* (2024.01)
*A01K 67/0275* (2024.01)
*C12N 15/85* (2006.01)

(52) U.S. Cl.
CPC ...... *A01K 67/0275* (2013.01); *C12N 15/8509* (2013.01); *A01K 2217/00* (2013.01); *A01K 2227/40* (2013.01); *A01K 2267/01* (2013.01)

(58) Field of Classification Search
None
See application file for complete search history.

(56) References Cited

U.S. PATENT DOCUMENTS

| | | |
|---|---|---|
| 7,135,613 B1 | 11/2006 | Gong et al. |
| 7,355,095 B2 | 4/2008 | Tsai et al. |
| 7,700,825 B2 | 4/2010 | Blake et al. |
| 7,834,239 B2 | 11/2010 | Gong et al. |
| 8,232,450 B1 | 7/2012 | Blake et al. |
| 8,232,451 B1 | 7/2012 | Blake et al. |
| 8,378,169 B2 | 2/2013 | Gong et al. |
| 8,581,025 B2 | 11/2013 | Blake et al. |
| 9,968,077 B2 | 5/2018 | Blake et al. |
| 10,798,923 B2 | 10/2020 | Blake et al. |
| 2002/0178461 A1 | 11/2002 | Lin |
| 2003/0162292 A1 | 8/2003 | Tsai et al. |
| 2004/0117866 A1 | 6/2004 | Tsai |
| 2004/0143864 A1 | 7/2004 | Gong et al. |
| 2005/0198701 A1 | 9/2005 | Lian et al. |
| 2005/0273874 A1 | 12/2005 | Tsai et al. |
| 2008/0052787 A1 | 2/2008 | Gong et al. |
| 2009/0025645 A1 | 1/2009 | Blake et al. |
| 2009/0035788 A1 | 2/2009 | Griesbeck et al. |
| 2009/0133138 A1 | 5/2009 | Tsai |
| 2009/0255006 A1 | 10/2009 | Dougan et al. |
| 2010/0037330 A1 | 2/2010 | Siripattarappavat et al. |
| 2010/0037331 A1 | 2/2010 | Blake et al. |
| 2010/0050280 A1 | 2/2010 | Blake et al. |
| 2010/0145889 A1 | 6/2010 | Blake et al. |
| 2012/0210453 A1 | 8/2012 | Blake et al. |
| 2012/0317665 A1 | 12/2012 | Blake et al. |
| 2013/0133093 A1 | 5/2013 | Blake et al. |
| 2013/0333060 A1 | 12/2013 | Blake et al. |
| 2014/0033338 A1 | 1/2014 | Blake et al. |
| 2014/0130195 A1 | 5/2014 | Blake et al. |
| 2015/0216148 A1 | 8/2015 | Blake et al. |
| 2015/0216149 A1 | 8/2015 | Blake et al. |
| 2015/0216150 A1 | 8/2015 | Blake et al. |
| 2015/0216151 A1 | 8/2015 | Blake et al. |
| 2016/0128310 A1 | 5/2016 | Blake et al. |
| 2017/0258057 A1 | 9/2017 | Blake et al. |
| 2020/0113159 A1 | 4/2020 | Blake et al. |
| 2020/0396972 A1 | 12/2020 | Blake et al. |
| 2021/0051927 A1 | 2/2021 | Blake et al. |
| 2022/0022432 A1 | 1/2022 | Blake et al. |
| 2022/0090126 A1 | 3/2022 | Blake et al. |

FOREIGN PATENT DOCUMENTS

| | | | |
|---|---|---|---|
| CN | 1590548 | * | 9/2005 |
| CN | 103540611 | | 1/2014 |
| CN | 103540611 A | | 1/2014 |

(Continued)

OTHER PUBLICATIONS

Fenner, The Rainbow, Redfin and Albino Minnow sharks *Epalzeorhynchos munense* and *E. frenatum*, The Conscientious Aquarist, WetWebMedia.com, (Year: 2022).*
Wikipedia description of rainbow shark (Year: 2007).*
Translation of CN 1590548 (Year: 2005).*
Vick B.M. et al., "Learning the scientific method using GloFish", Zebrafish, vol. 9(4): 226-241 (2012).
International Search Report and Written Opinion for PCT/US2019/061155, mailed Mar. 13, 2020.
International Search Report and Written Opinion for PCT/US2020/013102, mailed Jun. 19, 2020.
Berquand et al., "Analysis of Cytoskeleton-Destabilizing Agents by Optimized Optical Navigation and AFM Force Measurements," *Microscopy Today*, 18:34-37, 2010.
Day et al., "Fluorescent protein tools for studying protein dynamics in living cells: a review," *J Biomed Opt.*, 3(3):031202, 2008.
Finley et al., "Three-color imaging using fluorescent proteins in living zebrafish embryos," *Biotechniques*, 31(1):66-70; 72, 2001.

(Continued)

*Primary Examiner* — Michael C Wilson
(74) *Attorney, Agent, or Firm* — Dickinson Wright, PLLC

(57) ABSTRACT

The present invention relates to transgenic ornamental fish, as well as methods of making such fish by m vitro fertilization techniques. Also disclosed are methods of establishing a population of such transgenic fish and methods of providing them to the ornamental fish industry for the purpose of marketing.

9 Claims, No Drawings

(56) References Cited

FOREIGN PATENT DOCUMENTS

| CN | 106070063 | 11/2016 | | |
|---|---|---|---|---|
| CN | 106070063 A | 11/2016 | | |
| EP | 2166107 | 3/2010 | | |
| WO | WO 2000/049150 | 8/2000 | | |
| WO | WO 2008/022208 | 2/2008 | | |
| WO | WO-2008022208 A2 | * | 2/2008 | ........... A01K 67/027 |
| WO | WO 2009/148549 | 10/2009 | | |
| WO | 2018/183728 A1 | 10/2018 | | |

OTHER PUBLICATIONS

Franco et al., "Control of initial endothelial spreading by topographic activation of focal adhesion kinase," *Soft Matter.*, 77:313-7324, 2011.

Gong et al., "Development of transgenic fish for ornamental and bioreactor by strong expression of fluorescent proteins in the skeletal muscle," *Biochem. Bio phys. Res. Commun.*, 308(1):58-63, 2003.

Gong et al., "Green fluorescent protein (GFP) transgenic fish and their applications," *Genetica*, 111(1-3):213-25, 2001.

Ju et al., "Recapitulation of fast skeletal muscle development in zebrafish by transgenic expression of GFP under the mylz2 promoter," *Dev Dyn.*, 227(1):14-26, 2003.

Laranjeira et al., "Glial cells in the mouse enteric nervous system can undergo neurogenesis in response to injury," *J Clin Invest.*, 121(9):3412-24, 2011.

Liu et al., "Development of expression vectors for transgenic fish," *Biotechnology*, 8: 1268-1272, 1990.

Liu et al., "Isolation and characterization of beta-actin gene of carp (*Cyprinus carpio*)," *DNA Seq.*, 1(2):125-36, 1990.

Martynov et al., "Alternative cyclization in GFP-like proteins family," *The Journal of Biological Chemistry*, 276(24):21012-21016, 2001.

Nowotschin et al., "Live-imaging fluorescent proteins in mouse embryos: multi-dimensional, multi-spectral perspectives," *Trends in Biotechnology*, 27(5):266-276, 2009.

Parichy et al., "Zebrafish hybrids suggest genetic mechanisms for pigment pattern diversification in *Danio*," *Dev. Genes Evol.*, 211:319-328, 2001.

Shcherbo et al., "Bright far-red fluorescent protein for whole-body imaging," *Nature Methods*, 4(9):741-746, 2007.

Shkrob et al., "Far-red fluorescent proteins evolved from a blue chromoprotein from *Actinia equina*," *Biochem. J.*, 392:649-654, 2005.

Stewart, "Go with the glow: fluorescent proteins to light transgenic organisms," *Trends Biotechnol.*, 24(4):155-62, 2006.

Subach et al., "Conversion of red fluorescent protein into a bright blue probe," *Chemistry & Biology*, 15:1116-1124, 2008.

Urbani, "Multi-Color approach to track *Salmonella* during infection," *University of Basel, Master's Thesis*, pp. 1-35, Oct. 15, 2009.

Wan et al., "Generation of two-color transgenic zebrafish using the green and red fluorescent protein reporter genes gfp and rfp," *Mar Biotechnol (NY)*, 4(2)146-54, 2002.

Zhu et al., "Regulation of the lmo2 promoter during hematopoietic and vascular development in zebrafish," *Dev. Biol.*, 281(2):256-269, 2005.

Zhu et al., "Use of the DsRed fluorescent reporter in zebrafish," *Methods Cell. Biol.*, 76:3-12, 2004.

Design U.S. Appl. No. 29/501,874 entitled "Bright Red Fluorescent Tetra" by Alan Blake et al., filed Sep. 9, 2014.

Design U.S. Appl. No. 29/501,878 entitled "Bright Blue Fluorescent Tetra" by Alan Blake et al., filed Sep. 9, 2014.

Zhu Z. et al., Novel gene transfer into the fertilized eggs of gold fish (*Carassius auratus* L. 1758), Institute of Hydrobiology, Academia Sinica, Wuhan, P.R. China (1985).

Du S.J et al., "Growth enhancement in transgenic atlantic salmon by the use of an "All Fish" chimeric growth hormone gene contrust", Bio/Technology, Nature Publishing Group, vol. 10: 176-181 (1992).

Khoo H.W. et al., "Sperm cells as vectors for introducing foreign DNA into ebrafish", Aquaculture, 107, issue 1: 1-19 (1992).

Sin F.Y.T. et al., Gene transer in chinook salmon (*Oncorhynchus tshawytscha*) by electroporating sperm in the presence of pRSV-lacZ DNA, Aquaculture, 117: 57-69 (1993).

Zelenin A.V. et al., "The delivery of foreign genes into fertilized fish eggs using high-velocity microprojectiles", FEBS Lett. 287(1-2): 118-120 (1991).

Szelei J. et al., "Liposome-mediated gene transfer in fish embryos", Transgenic Research 3: 116-119 (1994).

Xu Y. et al., "Fast Skeletal Muscle-Specific Expression of a Zebrafish Myosin Light Chain 2 Gene and Characterization of Its Promoter by Direct Injection into Skeletal Muscle", DNA and Cell Biology, vol. 18: 85-95 (1999).

Chourrout D. et al., "High efficiency gene transfer in rainbow trout (*Salmo gardneri* Rich.) by microinjection into egg cytoplasm", Acuaculture, 51: 143-150 (1986).

Penman D.J. et al., "Factors Affecting Survival and Integration Following Microinjection of Novel DNA into Rainbor Trout Eggs", Aquaculture, 85: 35-50 (1990).

Brem G. et al., Gene Transfer in Tilapia (*Oreochromis nilotics*), Aquaculture 68: 209-219 (1988).

Gross M.L. et al., "Molecular analysis and growth evaluation of northern pike (*Esox lucius*) microinjected with growth hormone genes", Aquaculture, 103: 253-273 (1992).

Devlin R.H. et al., "Extraordinary salmon growth", Scientific Correspondence, Nature, vol. 371: 209-210 (1994).

Tsai H.J. et al., Electroporation of sperm to introduce foreign DNA into the genome of loach (*Misgurnus anguuillicauatus*): Can. J. Fish, Aquat. Sci. 52: 776-787 (1995).

Shagin et al., "GFP-like Proteins as Ubiquitous Metazoan Superfamily: Evolution of Functional Features and Structural Complexity", Molecular Biology and Evolution, vol. 21(5): 841-850 (2004).

C. Walker and G. Streisinger, Freezing Sperm in Zebrafish Book—A guide for the Laboratory Use of Zebrafish (*Danio rerio*) 4th Edition ZFIN: Breeding Zebrafish, University of Oregon (2016).

Draper et al., "A High-Throughput Method for Zebrafish Sperm Cryopreservation and In Vitro Fertilization", Journal pf Visualized Experiments, Jove, 29, e1395: 1-5 (2009).

International Search Report and Written Opinion for PCT/US2018/025224, mailed Jul. 6, 2018.

International Search Report and Written Opinion for PCT/US2019/013072, mailed Apr. 26, 2019.

* cited by examiner

TRANSGENIC RAINBOW SHARK

CROSS REFERENCE TO RELATED APPLICATIONS

This application is a National Stage application of PCT/US2019/013072, filed on Jan. 10, 2019, which claims priority to U.S. Provisional Patent Application No. 62/615,625, filed on Jan. 10, 2018 and entitled Transgenic Orange Rainbow Shark, and U.S. Provisional Patent Application No. 62/615,628, filed on Jan. 10, 2018 and entitled Transgenic Purple Rainbow Shark, and U.S. Provisional Patent Application No. 62/615,634, filed on Jan. 10, 2018 and entitled Transgenic Blue Rainbow Shark, and U.S. Provisional Patent Application No. 62/615,638, filed on Jan. 10, 2018 and entitled Transgenic Green Rainbow Shark. Each of the aforementioned references is incorporated herein by reference in its entirety. To the extent appropriate, a claim of priority is made to each of the above disclosed applications.

FIELD OF THE INVENTION

This invention relates to transgenic fish. Specifically, the invention relates to orange transgenic rainbow sharks. Specifically, the invention relates to purple transgenic rainbow sharks. Specifically, the invention relates to blue transgenic rainbow sharks. Specifically, the invention relates to green transgenic rainbow sharks.

INTRODUCTION

Transgenic technology involves the transfer of a foreign gene into a host organism enabling the host to acquire a new and inheritable trait. Transgenic technology has many potential applications. For example, it can be used to introduce a transgene into a fish in order to create new varieties of fish. There are many ways of introducing a foreign gene into fish, including: microinjection (e.g., Zhu et al., 1985; Du et al., 1992), electroporation (Powers et al., 1992), sperm-mediated gene transfer (Khoo et al., 1992; Sin et al., 1993), gene bombardment or gene gun (Zelenin et al., 1991), liposome-mediated gene transfer (Szelei et al., 1994), and the direct injection of DNA into muscle tissue (Xu et al., 1999). The first transgenic fish report was published by Zhu et al., (1985) using a chimeric gene construct consisting of a mouse metallothionein gene promoter and a human growth hormone gene. Most of the early transgenic fish studies have concentrated on growth hormone gene transfer with an aim of generating fast growing fish. While a majority of early attempts used heterologous growth hormone genes and promoters and failed to produce these fish (e.g. Chourrout et al., 1986; Penman et al., 1990; Brem et al., 1988; Gross et al., 1992), enhanced growth of transgenic fish has been demonstrated in several fish species including Atlantic salmon, several species of Pacific salmons, and loach (e.g. Du et al., 1992; Delvin et al., 1994, 1995; Tsai et al., 1995).

The rainbow shark (*Epalzeorhynchos frenatum*) is a freshwater cyprinid that comes from Thailand. While the fins possess red to orange-red coloration, the body varies from a black or dark gray to a lighter, almost silver color. The albino form lacks these darker spots, and the body color has a butter or pearl appearance. However, for the ornamental fish industry, the gray or pearl body does not aid in the efficient display of the various colors. The availability of such rainbow sharks having modified pigmentation for transgenesis with fluorescent proteins would result in better products for the ornamental fish industry due to better visualization of the various colors.

Many fluorescent proteins are known in the art and have been used to investigate various cellular processes, including fluorescent proteins exhibiting various green, yellow, orange, blue, or purple colors. Although transgenic experiments involving fluorescent proteins have provided new markers and reporters for transgenesis, progress in the field of developing and producing rainbow sharks that express such proteins has been limited.

Transgenic Rainbow Shark

In certain embodiments, the present disclosure concerns making transgenic fluorescent fish and providing such fish to the ornamental fish industry.

In some embodiments, transgenic fish or methods of making transgenic fish are provided. In certain aspects, the transgenic fish are fertile, transgenic, fluorescent fish. In a particular embodiment, the fish for use with the disclosed constructs and methods is the rainbow shark. Rainbow shark skin color is determined by pigment cells in the skin, which contain pigment granules called melanosomes (black or brown color), xanthosomes (yellow color), erythrosomes (orange or red color), or iridosomes (iridescent colors, including white color). The number, size, and density of the pigment granules per pigment cell influence the color of the fish skin.

In at least one example embodiment, there are provided transgenic rainbow shark or progeny thereof comprising specific transgenic integration events, referred to herein as transformation events. These fish are of particular interest because, for example, they embody an aesthetically pleasing orange color. Transgenic fish comprising these specific transgenic events may be homozygous or heterozygous (including, for example, hemizygous) for the transformation event. Homozygous fish bred with fish lacking a transformation event will in nearly all cases produce 100% heterozygous offspring. Eggs, sperm, and embryos comprising these specific transgenic events are also included as part of the invention.

In one such embodiment regarding a specific transgenic integration event, an orange transgenic rainbow shark or progeny thereof is provided comprising chromosomally integrated transgenes, wherein the rainbow shark comprises the "Orange rainbow shark 1 transformation event," sperm comprising the Orange rainbow shark 1 transformation event being deposited at the ECACC (Accession Number 19010802). The chromosomally integrated transgenes may be present on one integrated expression cassette or two or more integrated expression cassettes. In certain aspects, such a transgenic rainbow shark is a fertile, transgenic rainbow shark. Such a transgenic rainbow shark may be homozygous or heterozygous (including, for example, hemizygous) for the transgenes or integrated expression cassette(s).

Also disclosed are methods of providing a transgenic rainbow shark comprising the Orange rainbow shark 1 transformation event to the ornamental fish market. In some embodiments, the method comprises obtaining a transgenic rainbow shark or progeny thereof comprising chromosomally integrated transgenes, wherein the rainbow shark comprises the "Orange rainbow shark 1 transformation event," sperm comprising the Orange rainbow shark 1 transformation event being deposited at the ECACC (Accession Number 19010802), and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic rainbow shark are provided comprising: (a) obtaining a rainbow shark that exhibits fluorescence and comprises one or more chromosomally integrated transgenes or expression cassettes, wherein the rainbow shark comprises the "Orange rainbow shark 1 transformation event," sperm comprising the Orange rainbow shark 1 transformation event being deposited at the ECACC (Accession Number 19010802); and (b) breeding the obtained rainbow shark with a second rainbow shark to provide a transgenic rainbow shark comprising the Orange rainbow shark 1 transformation event. The second rainbow shark may be a transgenic or non-transgenic rainbow shark.

In further embodiments, also provided are methods of producing a transgenic organism, the method comprising using sperm comprising the Orange rainbow shark 1 transformation, such sperm being deposited at the ECACC (Accession Number 19010802), to produce transgenic offspring. Such offspring may be, for example, a rainbow shark, a species of the Cypriniformes family, a species of the *Epalzeorhynchos* genus, a fish species or genus related to rainbow shark, or another fish species or genus. In some aspects, the fish may be produced using in vitro fertilization techniques known in the art or described herein.

In at least one example embodiment, there are provided transgenic rainbow shark or progeny thereof comprising specific transgenic integration events, referred to herein as transformation events. These fish are of particular interest because, for example, they embody an aesthetically pleasing purple color. Transgenic fish comprising these specific transgenic events may be homozygous or heterozygous (including, for example, hemizygous) for the transformation event. Homozygous fish bred with fish lacking a transformation event will in nearly all cases produce 100% heterozygous offspring. Eggs, sperm, and embryos comprising these specific transgenic events are also included as part of the invention.

In one such embodiment regarding a specific transgenic integration event, a purple transgenic rainbow shark or progeny thereof is provided comprising chromosomally integrated transgenes, wherein the rainbow shark comprises the "Purple rainbow shark 1 transformation event," sperm comprising the Purple rainbow shark 1 transformation event being deposited at the ECACC (Accession Number 19010801). The chromosomally integrated transgenes may be present on one integrated expression cassette or two or more integrated expression cassettes. In certain aspects, such a transgenic rainbow shark is a fertile, transgenic rainbow shark. Such a transgenic rainbow shark may be homozygous or heterozygous (including, for example, hemizygous) for the transgenes or integrated expression cassette(s).

Also disclosed are methods of providing a transgenic rainbow shark comprising the Purple rainbow shark 1 transformation event to the ornamental fish market. In some embodiments, the method comprises obtaining a transgenic rainbow shark or progeny thereof comprising chromosomally integrated transgenes, wherein the rainbow shark comprises the "Purple rainbow shark 1 transformation event," sperm comprising the Purple rainbow shark 1 transformation event being deposited at the ECACC (Accession Number 19010801), and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic rainbow shark are provided comprising: (a) obtaining a rainbow shark that exhibits fluorescence and comprises one or more chromosomally integrated transgenes or expression cassettes, wherein the rainbow shark comprises the "Purple rainbow shark 1 transformation event," sperm comprising the Purple rainbow shark 1 transformation event being deposited at the ECACC (Accession Number 19010801); and (b) breeding the obtained rainbow shark with a second rainbow shark to provide a transgenic rainbow shark comprising the Purple rainbow shark 1 transformation event. The second rainbow shark may be a transgenic or non-transgenic rainbow shark.

In further embodiments, also provided are methods of producing a transgenic organism, the method comprising using sperm comprising the Purple rainbow shark 1 transformation, such sperm being deposited at the ECACC (Accession Number 19010801), to produce transgenic offspring. Such offspring may be, for example, a rainbow shark, a species of the Cypriniformes family, a species of the *Epalzeorhynchos* genus, a fish species or genus related to rainbow shark, or another fish species or genus. In some aspects, the fish may be produced using in vitro fertilization techniques known in the art or described herein.

In at least one example embodiment, there are provided transgenic rainbow shark or progeny thereof comprising specific transgenic integration events, referred to herein as transformation events. These fish are of particular interest because, for example, they embody an aesthetically pleasing blue color. Transgenic fish comprising these specific transgenic events may be homozygous or heterozygous (including, for example, hemizygous) for the transformation event. Homozygous fish bred with fish lacking a transformation event will in nearly all cases produce 100% heterozygous offspring. Eggs, sperm, and embryos comprising these specific transgenic events are also included as part of the invention.

In one such embodiment regarding a specific transgenic integration event, a blue transgenic rainbow shark or progeny thereof is provided comprising chromosomally integrated transgenes, wherein the rainbow shark comprises the "Blue rainbow shark 1 transformation event," sperm comprising the Blue rainbow shark 1 transformation event being deposited at the ECACC (Accession Number 19010803). The chromosomally integrated transgenes may be present on one integrated expression cassette or two or more integrated expression cassettes. In certain aspects, such a transgenic rainbow shark is a fertile, transgenic rainbow shark. Such a transgenic rainbow shark may be homozygous or heterozygous (including, for example, hemizygous) for the transgenes or integrated expression cassette(s).

Also disclosed are methods of providing a transgenic rainbow shark comprising the Blue rainbow shark 1 transformation event to the ornamental fish market. In some embodiments, the method comprises obtaining a transgenic rainbow shark or progeny thereof comprising chromosomally integrated transgenes, wherein the rainbow shark comprises the "Blue rainbow shark 1 transformation event," sperm comprising the Blue rainbow shark 1 transformation event being deposited at the ECACC (Accession Number 19010803), and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic rainbow shark are provided comprising: (a) obtaining a rainbow shark that exhibits fluorescence and comprises one or more chromosomally integrated transgenes or expression cassettes, wherein the rainbow shark comprises the "Blue rainbow shark 1 transformation event," sperm comprising the Blue rainbow shark 1 transformation event being deposited at the ECACC (Accession Number 19010803); and (b) breeding the obtained rainbow shark with a second rainbow shark to provide a transgenic rainbow shark comprising the Blue rainbow shark 1 transformation event. The second rainbow shark may be a transgenic or non-transgenic rainbow shark.

In further embodiments, also provided are methods of producing a transgenic organism, the method comprising using sperm comprising the Blue rainbow shark 1 transformation, such sperm being deposited at the ECACC (Accession Number 19010803), to produce transgenic offspring. Such offspring may be, for example, a rainbow shark, a species of the Cypriniformes family, a species of the *Epalzeorhynchos* genus, a fish species or genus related to rainbow shark, or another fish species or genus. In some aspects, the fish may be produced using in vitro fertilization techniques known in the art or described herein.

In at least one example embodiment, there are provided transgenic rainbow shark or progeny thereof comprising specific transgenic integration events, referred to herein as transformation events. These fish are of particular interest because, for example, they embody an aesthetically pleasing green color. Transgenic fish comprising these specific transgenic events may be homozygous or heterozygous (including, for example, hemizygous) for the transformation event. Homozygous fish bred with fish lacking a transformation event will in nearly all cases produce 100% heterozygous offspring. Eggs, sperm, and embryos comprising these specific transgenic events are also included as part of the invention.

In one such embodiment regarding a specific transgenic integration event, a green transgenic rainbow shark or progeny thereof is provided comprising chromosomally integrated transgenes, wherein the rainbow shark comprises the "Green rainbow shark 1 transformation event," sperm comprising the Green rainbow shark 1 transformation event being deposited at the ECACC (Accession Number 19010803). The chromosomally integrated transgenes may be present on one integrated expression cassette or two or more integrated expression cassettes. In certain aspects, such a transgenic rainbow shark is a fertile, transgenic rainbow shark. Such a transgenic rainbow shark may be homozygous or heterozygous (including, for example, hemizygous) for the transgenes or integrated expression cassette(s).

Also disclosed are methods of providing a transgenic rainbow shark comprising the Green rainbow shark 1 transformation event to the ornamental fish market. In some embodiments, the method comprises obtaining a transgenic rainbow shark or progeny thereof comprising chromosomally integrated transgenes, wherein the rainbow shark comprises the "Green rainbow shark 1 transformation event," sperm comprising the Green rainbow shark 1 transformation event being deposited at the ECACC (Accession Number 19010804), and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic rainbow shark are provided comprising: (a) obtaining a rainbow shark that exhibits fluorescence and comprises one or more chromosomally integrated transgenes or expression cassettes, wherein the rainbow shark comprises the "Green rainbow shark 1 transformation event," sperm comprising the Green rainbow shark 1 transformation event being deposited at the ECACC (Accession Number 19010804); and (b) breeding the obtained rainbow shark with a second rainbow shark to provide a transgenic rainbow shark comprising the Green rainbow shark 1 transformation event. The second rainbow shark may be a transgenic or non-transgenic rainbow shark.

In further embodiments, also provided are methods of producing a transgenic organism, the method comprising using sperm comprising the Green rainbow shark 1 transformation, such sperm being deposited at the ECACC (Accession Number 19010804), to produce transgenic offspring. Such offspring may be, for example, a rainbow shark, a species of the Cypriniformes family, a species of the *Epalzeorhynchos* genus, a fish species or genus related to rainbow shark, or another fish species or genus. In some aspects, the fish may be produced using in vitro fertilization techniques known in the art or described herein.

As used in this specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects. Any embodiment of any of the present methods, kits, and compositions may consist of or consist essentially of—rather than comprise/include/contain/have—the described features and/or steps.

Thus, in any of the claims, the term "consisting of" or "consisting essentially of" may be substituted for any of the open-ended linking verbs recited above, in order to change the scope of a given claim from what it would otherwise be using the open-ended linking verb. Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

Transgenic Fish

In some aspects, the present disclosure regards transgenic fish. Methods of making transgenic fish are described in, for example, U.S. Pat. Nos. 7,135,613; 7,700,825; 7,834,239, each of which is incorporated by reference in its entirety. For example, a transgenic orange rainbow shark may be generated using an expression cassette encoding yellow fluorescent protein (YFP), such as TurboYFP an enhanced variant of the yellow fluorescent protein PhiYFP from jellyfish *Phialidium* sp. (Shagin et al., 2004). In other examples, a transgenic purple rainbow shark may be generated using an expression cassette encoding purple fluorescent protein (PFP). In other examples, a transgenic blue rainbow shark may be generated using an expression cassette encoding blue fluorescent protein (BFP), such as TagBFP, or TagBFP in combination with Non-fluorescent blue chromoprotein. In other examples, a transgenic green rainbow shark may be generated using an expression cassette encoding green fluorescent protein (GFP), such as zsGreen1.

It is preferred that fish belonging to species and varieties of fish of commercial value, particularly commercial value within the ornamental fish industry, be used. Such fish include but are not limited to catfish, zebrafish and other danios, medaka, carp, tilapia, goldfish, tetras, barbs, sharks (family cyprinidae, such as rainbow shark), angelfish, loach, koi, glassfish, discus, eel, goby, gourami, guppy, Xiphophorus, hatchet fish, Molly fish, or pangasius. A particular fish for use in the context of the present disclosure is a rainbow shark, *Epalzeorhynchos frenatum*. Rainbow shark are increasingly popular ornamental animals and would be of added commercial value in various colors. Rainbow shark embryos are easily accessible and nearly transparent. Rainbow shark skin color is determined by pigment cells in the skin, which contain pigment granules called melanosomes. The number, size, and density of the melanosomes per pigment cell influence the color of the fish skin.

In Vitro Fertilization

In commercial aquaculture, rainbow sharks, including orange, purple, blue and green rainbow sharks, are not spawned naturally, but are spawned in vitro using the same, long-standing, industry-standard process that has been used for the reproduction of their non-fluorescent counterparts over the last several decades. At the same time, rainbow sharks are an ideal candidate for hormone induction as they are large enough to be easily handled and fecund, with females producing a substantial number of eggs per spawning. Generally speaking, rainbow sharks are seasonal breeders and can be most easily spawned from approximately May to October. It takes roughly one year for rainbow sharks to reach sexual maturity. One year-old females can release up to one thousand eggs per spawn, while older females can release up to 10,000 eggs per spawn if well-conditioned for breeding. Females can be spawned one or two times per season. Males can be spawned as frequently as two or three times per month. The most commonly used hormone for the induction of ovulation, which has been approved for use with ornamental fish by FDA, is called Ovaprim. It contains a salmonid gonadotropin-releasing hormone analog and a dopamine antagonist. Ovaprim produces consistent results, is easy to dose, and it is widely commercially available. Industry-standard breeding information for this species (for both the fluorescent and non-fluorescent phenotype) follows below, however, exact details may vary slightly from one producer to another.

Shark brood stock may be kept in indoor tanks, preferably with a volume of at least 300 gallons, but are typically conditioned outdoors in earthen ponds. Once conditioned for breeding, rainbow sharks are moved from outdoor, earthen ponds into large indoor holding vats. For breeding, conditioned brood stock are removed from the holding vat and placed in water containing a sedative, such as Tricaine, which is FDA approved for this type of use. Fish are considered to be adequately sedated when they roll over. At this time, the fish in question is removed from the water containing the sedative, weighed, and injected with Ovaprim. Males may also receive an Ovaprim injection to induce spermiation. Females will generally begin ovulation about seven hours after injection; once ovulation begins, eggs will flow freely when the fish are gently squeezed. To prepare for in vitro fertilization, the eggs should then be stripped into a dry bowl. A few drops of milt from male rainbow sharks should be similarly stripped into the same bowl. Stirring eggs and sperm together with 0.5 mL (approximately 10 drops) of water will begin the fertilization process. After 20 seconds, another 2 mL of water should be added. This process will cause the eggs to be fertilized within approximately 30 seconds. Once fertilized, eggs can be placed in McDonald-type egg hatching jars. The eggs will swell and become buoyant over the first 30 minutes, so the flow on the hatching jars should be adjusted to be as low as possible initially to avoid loss of the eggs. The flow should be checked frequently and adjusted as needed. Fry should be fed newly hatched Artemia nauplii on day two post-hatch, and they should continue to be fed Artemia for one week. From that point, they can begin the transition to a prepared diet, overlapping with live feed for 5 days. Two weeks post-hatch, the fry can be moved to vats and/or ponds for continued growth through maturity.

Fertilization from Frozen Sperm

Fish sperm freezing methods are well-known in the art; see, e.g., Walker and Streisinger (1983) and Draper and Moens (2007), both of which are incorporated herein by reference in their entireties. To obtain the transgenic fish disclosed herein, frozen rainbow shark sperm may be used to fertilize eggs.

In at least one method, conditioned females are removed from the holding vat and placed in water containing a sedative, such as Tricaine, which is FDA approved for this type of use. Fish are considered to be adequately sedated when they roll over. Once sedated, the subject fish is removed from the water containing the sedative, weighed, and injected with Ovaprim. Injected females will generally begin ovulation about seven hours after injection; once ovulation begins, eggs will flow freely when the fish are gently squeezed. To prepare for in vitro fertilization, the eggs should then be stripped into a dry bowl. Eggs from several females may be pooled; the eggs can be kept unfertilized for several minutes. Frozen sperm is thawed at 33° C. in a water bath for 18-20 seconds. Once the sperm is thawed 70 μL room temperature Hanks solution is added to the vial and mixed. The sperm is then immediately added to the eggs and gently mixed. Stirring eggs and sperm together with 0.5 mL (approximately 10 drops) of water will begin the fertilization process. After 20 seconds, another 2 mL of water should be added. This process will cause the eggs to be fertilized within approximately 30 seconds. Once fertilized, eggs can be placed in McDonald-type egg hatching jars. The eggs will swell and become buoyant over the first 30 minutes, so the flow on the hatching jars should be adjusted to be as low as possible initially to avoid loss of the eggs. The flow should be checked frequently and adjusted as needed. Fry should be fed newly hatched Artemia nauplii on day two post-hatch, and they should continue to be fed Artemia for one week. After the first week post hatch, fry can begin the transition to a prepared diet, overlapping with live feed for 5 days. Two weeks post-hatch, the fry can be moved to vats and/or ponds for continued growth through maturity. Parichy and Johnson, 2001, which is incorporated by reference in its entirety, provides additional examples regarding in vitro fertilization.

The present disclosure further encompasses progeny of a transgenic fish containing the Orange rainbow shark 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The second fish may be of the same species, or may be of a different species or genus. The hybrid progeny of these matings have the benefits of the transgene for fluorescence combined with the benefits derived from these other lineages.

The simplest way to identify fish containing the Orange rainbow shark 1 transformation event is by visual inspection, as the fish in question would be orange colored and immediately distinguishable from non-transgenic fish.

The present disclosure further encompasses progeny of a transgenic fish containing the Purple rainbow shark 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The second fish may be of the same species, or may be of a different species or genus. The hybrid progeny of these matings have the benefits of the transgene for fluorescence combined with the benefits derived from these other lineages.

The simplest way to identify fish containing the Purple rainbow shark 1 transformation event is by visual inspection, as the fish in question would be purple colored and immediately distinguishable from non-transgenic fish.

The present disclosure further encompasses progeny of a transgenic fish containing the Blue rainbow shark 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The second fish may be of the same species, or may be of a different species or genus. The hybrid progeny of these matings have the benefits of the transgene for fluorescence combined with the benefits derived from these other lineages.

The simplest way to identify fish containing the Blue rainbow shark 1 transformation event is by visual inspection, as the fish in question would be blue colored and immediately distinguishable from non-transgenic fish.

The present disclosure further encompasses progeny of a transgenic fish containing the Green rainbow shark 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The second fish may be of the same species, or may be of a different species or genus. The hybrid progeny of these matings have the benefits of the transgene for fluorescence combined with the benefits derived from these other lineages.

The simplest way to identify fish containing the Green rainbow shark 1 transformation event is by visual inspection, as the fish in question would be green colored and immediately distinguishable from non-transgenic fish.

EXAMPLES

Certain embodiments of the invention are further described with reference to the following examples. These examples are intended to be merely illustrative of the invention and are not intended to limit or restrict the scope of the present invention in any way and should not be construed as providing conditions, parameters, reagents, or starting materials that must be utilized exclusively in order to practice the art of the present invention.

Example 1—Orange Transgenic Rainbow Shark

Transgenic fish exhibiting an orange color are provided. The specific transgenic events embodied in these fish are designated the "Orange rainbow shark 1 transformation event". Sperm from these fish may be used to fertilize rainbow shark eggs and thereby breed transgenic rainbow shark that comprise these specific transgenic integration events. Sperm from this line was deposited at the European Collection of Cell Cultures (ECACC (Accession Number 19010802)), Public Health England, CRYOSTORES, Bld. 17, Porton Down, Salisbury, SP4 OJG, United Kingdom, under the provisions of the Budapest Treaty as "Orange rainbow shark 1".

Example 2—Purple Transgenic Rainbow Shark

Transgenic fish exhibiting a purple color are provided. The specific transgenic events embodied in these fish are designated the "Purple rainbow shark 1 transformation event". Sperm from these fish may be used to fertilize rainbow shark eggs and thereby breed transgenic rainbow shark that comprise these specific transgenic integration events. Sperm from this line was deposited at the European Collection of Cell Cultures (ECACC (Accession Number 19010801)), Public Health England, CRYOSTORES, Bld. 17, Porton Down, Salisbury, SP4 OJG, United Kingdom, under the provisions of the Budapest Treaty as "Purple rainbow shark 1".

Example 3—Blue Transgenic Rainbow Shark

Transgenic fish exhibiting a blue color are provided. The specific transgenic events embodied in these fish are designated the "Blue rainbow shark 1 transformation event". Sperm from these fish may be used to fertilize rainbow shark eggs and thereby breed transgenic rainbow shark that comprise these specific transgenic integration events. Sperm from this line was deposited at the European Collection of Cell Cultures (ECACC (Accession Number 19010803)), Public Health England, CRYOSTORES, Bld. 17, Porton Down, Salisbury, SP4 OJG, United Kingdom, under the provisions of the Budapest Treaty as "Blue rainbow shark 1".

Example 4—Green Transgenic Rainbow Shark

Transgenic fish exhibiting a green color are provided. The specific transgenic events embodied in these fish are designated the "Green rainbow shark 1 transformation event". Sperm from these fish may be used to fertilize rainbow shark eggs and thereby breed transgenic rainbow shark that comprise these specific transgenic integration events. Sperm from this line was deposited at the European Collection of Cell Cultures (ECACC (Accession Number 19010804)), Public Health England, CRYOSTORES, Bld. 17, Porton Down, Salisbury, SP4 OJG, United Kingdom, under the provisions of the Budapest Treaty as "Green rainbow shark 1".

The fluorescent transgenic fish have use as ornamental fish in the market. Stably expressing transgenic lines can be developed by breeding a transgenic individual with a wild-type fish, mutant fish, or another transgenic fish. The desired transgenic fish can be distinguished from non-transgenic fish by observing the fish in white light, sunlight, ultraviolet light, blue light, or any other useful lighting condition that allows visualization of the orange, purple, green or blue color of the transgenic fish.

The fluorescent transgenic fish should also be valuable in the market for scientific research tools because they can be used for embryonic studies such as tracing cell lineage and cell migration. Additionally, these fish can be used to mark cells in genetic mosaic experiments and in fish cancer models.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. A transgenic rainbow shark sperm whose genome comprises:
    a) an exogenous nucleic sequence encoding an orange fluorescent protein, wherein the transgenic rainbow shark sperm is deposited at the European Collection of Authenticated Cell Cultures (ECACC) as Accession Number 19010802;
    b) an exogenous nucleic sequence encoding a purple fluorescent protein, wherein the transgenic rainbow shark sperm is deposited at the ECACC as Accession Number 19010801;
    c) an exogenous nucleic sequence encoding a blue fluorescent protein, wherein the transgenic rainbow shark sperm is deposited at the ECACC as Accession Number 19010803; or
    d) an exogenous nucleic sequence encoding a green fluorescent protein, wherein the transgenic rainbow shark sperm is deposited at the ECACC as Accession Number 19010804.

2. A method of making a transgenic rainbow shark the method comprising:
    (a) fertilizing a rainbow shark egg with the sperm of claim 1 such that a transgenic shark whose genome comprises a nucleic acid sequence encoding an orange, purple, blue, or green fluorescent protein is obtained, wherein the transgenic rainbow shark functionally expresses the orange, purple, blue, or green fluorescent protein.

3. The method of claim 2, wherein the rainbow shark egg is non-transgenic.

4. A transgenic rainbow shark whose genome comprises a nucleic acid sequence encoding an orange, purple, blue, or green fluorescent protein obtained from the method of claim 2, wherein the transgenic rainbow shark functionally expresses the orange, purple, blue, or green fluorescent protein.

5. The transgenic rainbow shark of claim 4, wherein the shark is fertile.

6. A method of providing a transgenic rainbow shark to the ornamental fish market, comprising producing a transgenic rainbow shark with the method of claim 2, and distributing the fish to the ornamental fish market.

7. The method of claim 6, wherein the fish are distributed by a grower to a commercial distributor.

8. The method of claim 6, wherein the fish are distributed by a grower or a commercial distributor to a retailer.

9. The method of claim 8, wherein the retailer is a multi-product retailer having an ornamental fish department.

* * * * *